(12) United States Patent
Maianti et al.

(10) Patent No.: US 7,063,816 B2
(45) Date of Patent: Jun. 20, 2006

(54) HEMOCONCENTRATOR IN EXTRACORPOREAL BLOOD CIRCUIT

(75) Inventors: Edgardo Costa Maianti, Mirandola (IT); Nicola Ghelli, San Pietro in Casale (IT); Ivo Panzani, Mirandola (IT); Gabriele Tommasi, Cavezzo (IT)

(73) Assignee: Sorin Group Italia S.r.l., Mirandola (IT)

( * ) Notice: Subject to any disclaimer, the term of this patent is extended or adjusted under 35 U.S.C. 154(b) by 535 days.

(21) Appl. No.: 10/614,721

(22) Filed: Jul. 7, 2003

(65) Prior Publication Data
US 2004/0054314 A1   Mar. 18, 2004

(30) Foreign Application Priority Data
Jul. 15, 2002 (IT) ............................ MI2002A1553

(51) Int. Cl.
*A61M 1/14* (2006.01)
*A61M 37/00* (2006.01)
*A61B 19/00* (2006.01)
*C02F 1/44* (2006.01)
*B01D 11/04* (2006.01)

(52) U.S. Cl. ............. 422/44; 604/4.01; 604/5.01; 604/6.01; 604/6.15; 604/403; 210/634; 210/645; 210/321.6

(58) Field of Classification Search ............... 604/4.01, 604/5.01, 6.01–6.07, 6.09, 6.1, 6.11, 6.14–6.16, 604/7, 403, 406, 408–410; 128/DIG. 28; 422/44–48; 210/636, 637, 645, 646, 650, 210/651, 634, 805
See application file for complete search history.

(56) References Cited

U.S. PATENT DOCUMENTS

| 4,800,022 A * | 1/1989 | Leonard ...................... 210/636 |
| 6,193,681 B1 * | 2/2001 | Davidner et al. .......... 604/6.08 |
| 6,342,157 B1 * | 1/2002 | Hood, III ................ 210/321.6 |

FOREIGN PATENT DOCUMENTS

| EP | 0 705 610 A1 * | 10/1994 |
| EP | 0 705 610 A1 | 4/1996 |
| EP | 0 820 775 A2 | 1/1998 |
| EP | 0 820 775 A3 | 2/1998 |
| WO | WO 97/32653 | 9/1997 |

OTHER PUBLICATIONS

European Search Report for counterpart Application No. 03015534.5 (3 pages).

* cited by examiner

*Primary Examiner*—Patricia Bianco
(74) *Attorney, Agent, or Firm*—Popovich, Wiles & O'Connell, P.A.

(57) ABSTRACT

A device for treating blood in an extracorporeal circuit comprising a venous blood reservoir having an inlet and an outlet, and a hemoconcentrator having a first inlet connector for the blood to be treated, a second outlet connector for the outflow of concentrated blood, and a third outlet connector for the outflow of the ultrafiltered liquid, wherein the hemoconcentrator is disposed within the venous blood reservoir and the hemoconcentrator and the venous blood reservoir are integrated into a single monolithic assembly, and wherein the hemoconcentrator comprises an enclosure containing structure suitable to concentrate blood.

6 Claims, 2 Drawing Sheets

HEMOCONCENTRATOR IN EXTRACORPOREAL BLOOD CIRCUIT

FIELD OF THE INVENTION

The invention relates to a hemoconcentrator in an extracorporeal blood circuit.

BACKGROUND OF THE INVENTION

It is known that during certain surgical procedures it is necessary to establish an extracorporeal circulation of the blood of the patient in a circuit that comprises devices suitable to ensure correct treatment of the blood. Such devices comprise at least one reservoir for containing the blood, termed venous blood, that leaves the patient, a pump for conveying the blood in the circuit, a heat exchanger in which the blood encounters a heat exchange fluid that ensures its correct temperature, an oxygenation apparatus meant to transfer oxygen to the blood, and finally a filter that is interposed on the line, known as the arterial blood line, that returns the blood to the patient, with the purpose of retaining any air bubbles that are present in the blood. The described extracorporeal circuit is completed by the presence of a container for the blood collected by salvage from the operating field, know as a cardiotomy reservoir, which is connected to the venous blood reservoir.

In addition to the described devices, in the described circuit there is also often a hemoconcentrator, to which a portion of the blood that flows in the circuit is fed, if required, in order to be concentrated. The hemoconcentrator comprises an enclosure for containing the structure suitable to concentrate the blood. Such structures include a bundle of capillary fibers that are meant to be crossed by the blood and allow ultrafiltered liquid to exit from their walls, consequently concentrating the blood. The conditions of the ultrafiltration depend on the transmembrane pressure, which is the average of the input and output pressures of the blood and can be changed by virtue of devices for throttling the line that conveys the concentrated blood in output.

In the art, the hemoconcentrator is an independent element that is connected to a point of the circuit by a blood supply line and is provided with a line for conveying the concentrated blood in output to the venous blood reservoir, and this fact produces some disadvantageous characteristics that prevent full optimization of the blood treatment conditions.

SUMMARY OF THE INVENTION

The aim of the present invention is therefore to provide a hemoconcentrator that minimizes the filling volume, i.e., the volume of the blood outside the body of the patient, the surface in contact with the blood, and the overall dimensions, so as to ensure optimum blood treatment and convenient management by operators.

The proposed aim can be achieved by a hemoconcentrator in an extracorporeal blood circuit. The circuit comprises a venous blood reservoir that receives the blood that arrives from the patient. The hemoconcentrator comprises an enclosure for containing a structure suitable to concentrate the blood, and is provided with a first inlet connector for the blood to be treated, which is drawn by means of a line provided with an occlusion structure from the blood circuit. The hemoconcentrator is also provided with a second connector for the outflow of the concentrated blood and with a third connector for the outflow of the ultrafiltered liquid. The third connector for the outflow of the ultrafiltered liquid is connected by a line to a disposal bag. The enclosure is inserted monolithically within the venous blood reservoir so that the concentrated blood outflow connector leads to a port that is connected to the reservoir. The enclosure is provided with a flow control element that is suitable to be actuated by an operator in order to vary the passage section of the blood through the port. The flow control element comprises a duct that is open at one end onto the second connector for the outflow of the concentrated blood and is connected at the other end to the disposal bag by a line provided with an occlusion structure.

The invention provides a device for treating blood in an extracorporeal circuit comprising a venous blood reservoir having an inlet and an outlet, and a hemoconcentrator having a first inlet connector for the blood to be treated, a second outlet connector for the outflow of concentrated blood, and a third outlet connector for the outflow of the ultrafiltered liquid, wherein the hemoconcentrator is disposed within the venous blood reservoir and the hemoconcentrator and the venous blood reservoir are integrated into a single monolithic assembly, and wherein the hemoconcentrator comprises an enclosure containing structure suitable to concentrate blood.

Additional features and advantages of the invention are set forth in the description which follows and in part will be apparent from the description. The objectives and other advantages of the invention will be realized and attained by the device as particularly pointed out in the written description and claims.

It is to be understood that both the foregoing general description and the following detailed description are exemplary and explanatory and are intended to provide further explanation of the invention as claimed.

BRIEF DESCRIPTION OF THE DRAWING

Further characteristics and advantages will become apparent from the description of a preferred but not exclusive embodiment of the invention, which are illustrated by way of non-limitative example in the accompanying drawings.

BRIEF DESCRIPTION OF THE PREFERRED EMBODIMENTS

Figure 1:
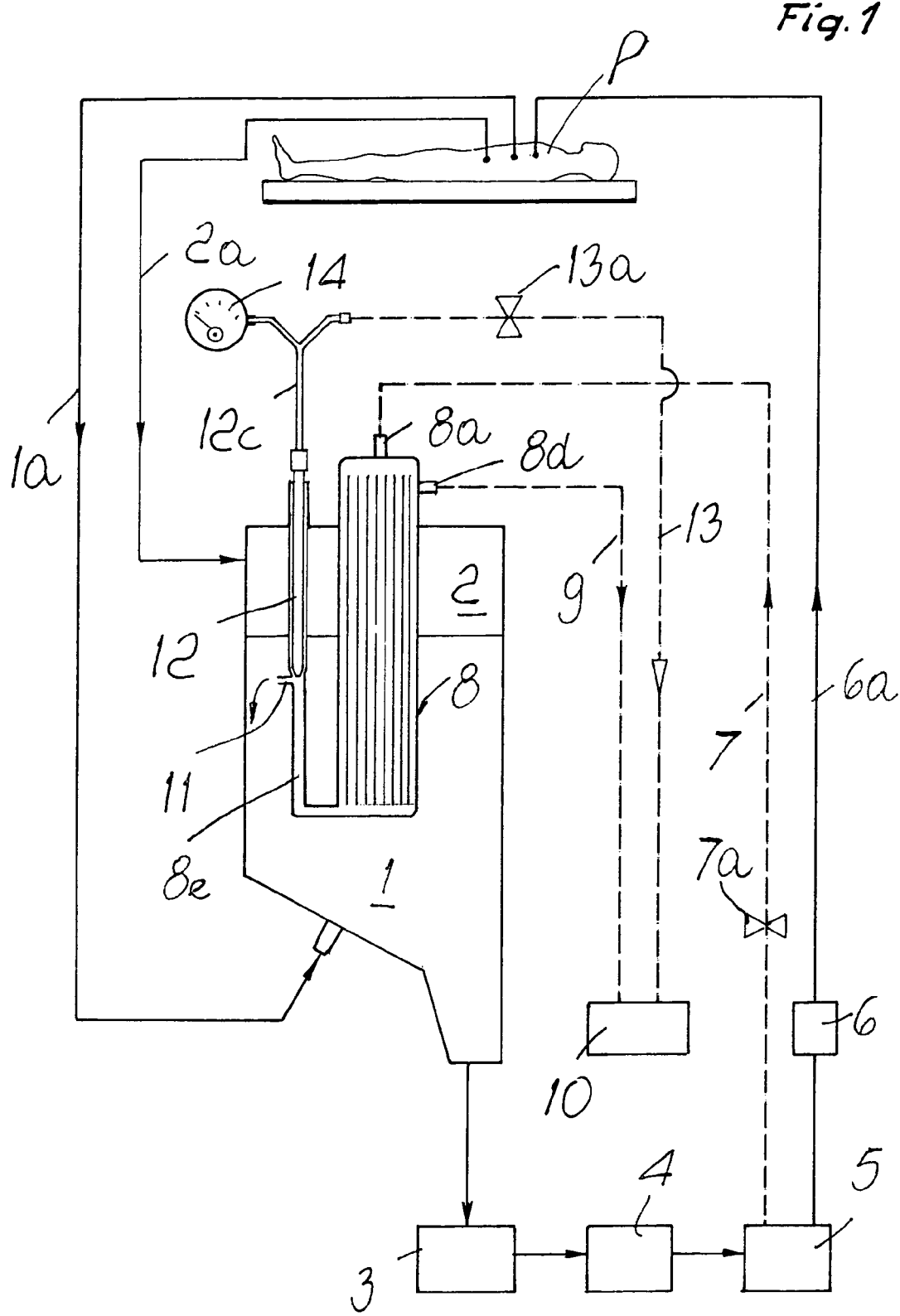
FIG. 1 is a schematic view of an extracorporeal blood circuit comprising a hemoconcentrator according to the invention.

The main blood circuit shown in FIG. 1 comprises a series of devices connected by virtue of connecting lines, which are shown in solid lines. The blood is drawn from patient P by means of the venous blood line 1a and is introduced in the venous blood reservoir 1, in which the cardiotomy reservoir 2 is integrated and interconnected in an upward region. The cardiotomy reservoir receives, through line 2a, blood recovered from the operating field (i.e., from the patient). The blood then passes to pump 3, to heat exchanger 4, to oxygenation apparatus 5, and returns to the patient by means of arterial blood line 6a, with interposed arterial blood filter 6.

Figure 2:
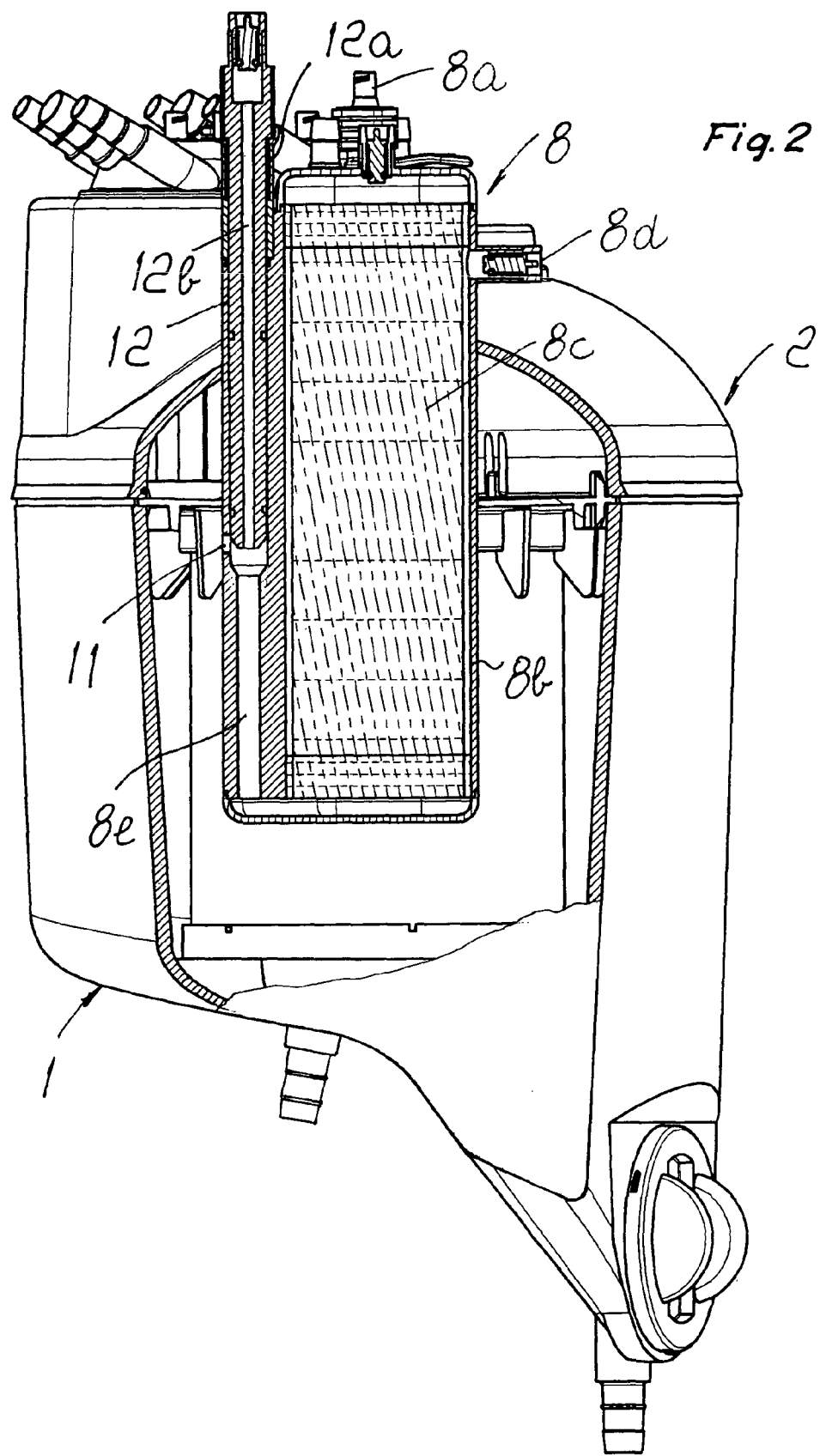
FIG. 2 is a side view of the venous reservoir showing a partial cross-sectional view of the hemoconcentrator integrated into the venous reservoir according to the invention.

If necessary, a portion of blood is drawn from the described circuit, and more specifically from oxygenation apparatus 5 of the circuit, and by line 7 provided with occlusion structure 7a is sent to inlet connector 8a of hemoconcentrator 8, which according to an important characteristic of the invention has enclosure 8b for containing blood concentration structure 8c inserted monolithically in venous blood reservoir 1. See FIG. 2. Enclosure 8b is provided with outlet connector 8d for the ultrafiltered liquid, which is connected by line 9 to disposal bag 10, and with connector 8e for the outflow of the concentrated blood, which leads to port 11, which is directly connected to the inside of venous blood reservoir 1.

The numeral 12 designates a flow control element that is associated with the enclosure 8b by a threaded portion 12a and can be actuated by an operator by gripping the upper end portion that protrudes from the enclosure 8b, so as to be arranged at a variable level so as to vary the passage section of the blood through port 11 and thereby the load loss affecting the blood in output. The described flow control element 12 comprises internally duct 12b, which is open at one end on connector 8e and is connected at the other end to disposal bag 10 by line 13, which is provided with occlusion structure 13a and leads out from connector 12c, which is associated with the upper end of flow control element 12. Finally, reference numeral 14 designates a pressure gauge that is connected to connector 12c.

As regards the operation of the invention, it should be noted first of all that, as noted earlier, by screwing and unscrewing flow control element 12, the operator also varies, together with the passage section for the blood through port 11, the load loss encountered by the blood in output. The resulting variation of the transmembrane pressure of the blood inside the hemoconcentrator results in variations of the ultrafiltration conditions that occur in the hemoconcentrator.

However, another important functional condition of the invention should now be highlighted. The step for filling the circuit by means of physiological solution, known as priming, is performed while occlusion structure 7a of line 7 is open and while port 11 and occlusion structure 13a of line 13 are closed. This arrangement results in the filling of the hemoconcentrator 8 with physiological solution. In the normal operation of the extracorporeal blood circuit connected to the patient, hemoconcentrator 8 is excluded by closing occlusion structure 7a of line 7.

When one wishes to concentrate a portion of blood sent to hemoconcentrator 8 by line 7, occlusion structures 7a and 13a are opened and port 11 is kept closed; the incoming blood immediately pushes in front of itself the physiological solution contained in hemoconcentrator 8, sending it to disposal bag 10. When hemoconcentrator 8 is completely emptied of physiological solution and filled with blood, occlusion structure 13a is closed. By actuating flow control element 12, port 11 is opened in order to produce the conditions of normal operation without any dilution of the blood caused by introduction of physiological solution in the venous blood reservoir.

Attention should now be called to the fact that an embodiment of the invention has been described in which venous blood reservoir 1 is inserted in an extracorporeal circuit and the individual devices are provided as independent elements connected by virtue of connection lines. Obviously, nothing changes if the venous blood reservoir is integrated in a single unit with the other devices of the circuit, for example of the type disclosed in a co-pending, commonly assigned patent application Ser. No. 10/614,722, filed on even date herewith, entitled "Device for Treating Blood in an Extracorporeal Circuit" (Costa Maianti et al.), hereby incorporated herein by reference in its entirety.

The above description and accompanying drawings are provided for the purpose of describing embodiments of the invention and are not intended to limit the scope of the invention in any way. It will be apparent to those skilled in the art that various modifications and variations can be made in the device without departing from the spirit or scope of the invention. Thus, for example, flow control element 12 can have various positions on the enclosure of the hemoconcentrator. Port 11, instead of being connected to the inside of venous blood reservoir 1, can exit cardiotomy reservoir 2, thus being indirectly connected to the venous blood reservoir. Thus, it is intended that the present invention cover the modifications and variations of this invention provided they come within the scope of the appended claims and their equivalents.

What is claimed is:

1. A device for treating blood in an extracorporeal circuit comprising a venous blood reservoir having an inlet and an outlet, and a hemoconcentrator having a first inlet connector for the blood to be treated, a second outlet connector for the outflow of concentrated blood, and a third outlet connector for the outflow of the ultrafiltered liquid, wherein the hemoconcentrator is disposed within the venous blood reservoir and the hemoconcentrator and the venous blood reservoir are integrated into a single monolithic assembly, and wherein the hemoconcentrator comprises an enclosure containing structure suitable to concentrate blood.

2. The device according to claim 1, wherein the second outlet connector leads to a port that is connected to the venous reservoir and the second outlet connector is provided with a flow control element that is suitable to be actuated by an operator in order to vary the passage section of the blood through the port, and wherein the flow control element comprises a duct that is open at one end onto the second outlet connector and is suitable to be connected at the other end to a disposal bag by a line provided with an occlusion structure.

3. The device according to claim 2, wherein the second outlet connector leads to a port that is directly connected to the venous blood reservoir.

4. The device according to claim 2, wherein the flow control element is associated with the enclosure of the hemoconcentrator by a threaded portion.

5. The device according to claim 1, wherein the second outlet connector leads to a port that is connected to a cardiotomy reservoir that is associated with the venous blood reservoir and is connected thereto, and the second outlet connector is provided with a flow control element that is suitable to be actuated by an operator in order to vary the passage section of the blood through the port, and wherein the flow control element comprises a duct that is open at one end onto the second outlet connector and is suitable to be connected at the other end to a disposal bag by a line provided with an occlusion structure.

6. The device according to claim 5, wherein the flow control element is associated with the enclosure of the hemoconcentrator by a threaded portion.

* * * * *